United States Patent [19]

Chan

[11] Patent Number: 4,460,603

[45] Date of Patent: Jul. 17, 1984

[54] 1-(2'-HALOALKYL)-AMIDOMETHYL-SUBSTITUTED ACETANILIDE FUNGICIDES

[75] Inventor: David C. K. Chan, Petaluma, Calif.

[73] Assignee: Chevron Research Company, San Francisco, Calif.

[21] Appl. No.: 280,653

[22] Filed: Jul. 6, 1981

Related U.S. Application Data

[63] Continuation-in-part of Ser. No. 207,106, Nov. 17, 1980, abandoned.

[51] Int. Cl.$^3$ ..................... A01N 37/22; C07C 103/82
[52] U.S. Cl. .................... 424/324; 260/454; 260/455 R; 260/465 D; 424/270; 424/272; 424/273 R; 424/273 P; 424/283; 424/285; 424/301; 424/302; 424/304; 424/309; 424/311; 548/200; 548/214; 548/236; 548/248; 548/343; 548/378; 549/357; 549/372; 549/378; 549/487; 549/548; 560/10; 560/16; 560/43; 560/227; 560/228; 564/74; 564/155; 564/158; 564/154

[58] Field of Search ............... 260/347.2, 347.3, 347.4, 260/454, 455 R, 465 D; 424/285, 301, 302, 304, 305, 309, 324; 560/227, 228, 43; 564/74, 154, 155, 158; 549/487

[56] References Cited

U.S. PATENT DOCUMENTS

| | | | |
|---|---|---|---|
| 4,025,648 | 5/1977 | Hubele | 424/309 |
| 4,032,657 | 6/1977 | Moser | 424/309 |
| 4,034,108 | 7/1977 | Moser | 424/309 |
| 4,093,738 | 6/1978 | Hubele | 424/309 |
| 4,094,990 | 6/1978 | Hubele | 424/285 |
| 4,151,299 | 4/1979 | Hubele | 424/309 |
| 4,275,079 | 6/1981 | Dorn | 424/324 |

FOREIGN PATENT DOCUMENTS 28011 6/1981 European Pat. Off. .

*Primary Examiner*—Richard Raymond
*Attorney, Agent, or Firm*—S. R. LaPaglia; T. G. DeJonghe; L. S. Squires

[57] ABSTRACT

N-[1-(2'-substituted-alkyl)-amidomethyl and carboalkoxymethyl]-substituted-N-acylanilines have fungicidal activity.

7 Claims, No Drawings

1-(2'-HALOALKYL)-AMIDOMETHYL-SUBSTITUTED ACETANILIDE FUNGICIDES

RELATED APPLICATIONS

This application is a continuation-in-part of copending application Ser. No. 207,106, filed Nov. 17, 1980, now abandoned.

BACKGROUND OF THE INVENTION

The U.S. Pat. Nos. 4,034,108, 4,025,648 and 4,032,657 disclosed N-(1'-methyl-carbalkoxymethyl) acetanilides having fungicidal activity. U.S. Pat. Nos. 4,151,299, 4,093,738 and 4,094,990 disclose N-(1'-methyl-carbalkoxy)-1-alkoxy-acetanilides having fungicidal activity.

SUMMARY OF THE INVENTION

I have found that certain 1-(2'-haloalkyl)amidomethyl-substituted acetanilides are effective for the control of fungi, especially for downy mildew fungal infections caused by Peronosporaceae and late blight fungal infection caused by *Phytophthora infestans*. Some of the compounds of the invention are effective both as protective fungicides, i.e., they prevent or protect against fungal infections, and as eradicant fungicides, i.e., they eliminate and cure established infections. Surprisingly, the compounds of the invention are particularly more effective for the control of grape downy mildew and tomato late blight than the compounds previously disclosed in the aforementioned patents.

DESCRIPTION OF THE INVENTION

The compounds of the invention are represented by the formula I:

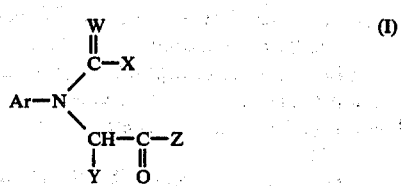

wherein Ar is

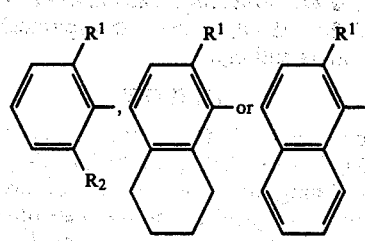

wherein $R^1$ and $R^2$ are independently alkyl or alkoxy of 1 to 4 carbon atoms or halo;

X is alkyl of 1 to 6 carbon atoms, haloalkyl of 1 to 6 carbon atoms and 1 to 4 halogen atoms, alkoxyalkyl of 2 to 12 carbon atoms, alkylthioalkyl of 2 to 12 carbon atoms, alkenyl of 3 to 6 carbon atoms, alkynyl of 3 to 6 carbon atoms, haloalkenyl of 3 to 6 carbon atoms and 1 to 3 halogen atoms, haloalkynyl of 3 to 6 carbon atoms and 1 to 3 halogen atoms, hydroxyalkyl of 1 to 4 carbon atoms, cycloalkyl of 3 to 6 carbon atoms, oxiranyl ring of 2 to 6 carbon atoms, or a three, four, five or six-membered heterocyclic ring of the formula containing one or two heteroatoms selected from nitrogen, sulfur and oxygen; Y is a 2-haloalkyl group of 2 to 6 carbon atoms, a 2-hydroxyalkyl group of 2 to 6 carbon atoms, a 2-alkoxyalkyl group of 3 to 6 carbon atoms, a 2-(alkylthio)alkyl group of 3 to 6 carbon atoms, a 2-cyanoalkyl group, a 2-(thiocyano)alkyl group of 3 to 6 carbon atoms, or a haloalkylcarboxyalkyl group of 2 to 6 carbon atoms and 1 to 4 halogen atoms; W is oxygen or sulfur.

Z is an alkoxy group of 1 to 6 carbon atoms, alkylthio group of 1 to 6 carbon atoms or a $-NR^4R^5$ group wherein $R^4$ is hydrogen, alkyl of 1 to 4 carbon atoms, alkenyl of 2 to 4 carbon atoms or alkynyl of 2 to 4 carbon atoms and $R^5$ is hydrogen, or alkyl of 1 to 4 carbon atoms.

Representative groups which Ar may be are 2-fluorophenyl, 2,6-diethylphenyl, 2-methoxyphenyl, 2,6-dimethylphenyl, 2-methyl-naphth-1-yl, 2-chloronaphth-1-yl, 2-chloro-naphth-1-yl, 5,6,7,8-tetrahydro-2-methylnaphth-1-yl. Most preferred Ar groups are 2,6-dialkylphenyl, especially 2,6-dimethylphenyl.

Representative groups for X are chloromethyl, bromomethyl, 2-bromoethyl, 2,2,2-trifluoroethyl, methoxymethyl, ethoxymethyl, 2-methoxyethyl, methylthioethyl, methylthiomethyl, ethylthioethyl, vinyl, 2-methyl-vinyl, 2,2,-dimethylvinyl, 1-methylvinyl, allyl, isopropenyl, butenyl, propargyl, 4-chloro-1-butenyl, 3-chloropropargyl, hydroxymethyl, 2-hydroxyethyl, cyclopropyl, cyclobutyl, cyclopentyl, cyclohexyl, oxiranyl, 1-methyloxirane-1-yl, 2,2-dimethyloxirane-1-yl, 2-methyloxirane-1-yl, thiazolyl, diazolyl, oxazolyl, dioxanyl or furanyl. Preferably, X is haloalkyl of 1 to 6 carbon atoms and 1 to 4 halogen atoms or alkoxyalkyl of 2 to 12 carbon atoms. More preferably, X is alkoxyalkyl of 2 to 12 carbon atoms, most preferably, methoxymethyl.

Representative groups for Y are 2-chloroethyl, 2-bromoethyl, 2-chloropropyl, 2-chlorobutyl, 2-bromopentyl, 2-bromohexyl, 2-hydroxyethyl, 2-hydroxypropyl, 2-hydroxybutyl, 2-hydroxyhexyl, 2-methoxyethyl, 2-methoxypropyl, 2-ethoxypropyl, 2-(methylthio)ethyl, 2-(methylthio)propyl, 2-(ethylthio)ethyl, 2-(ethylthio)butyl, 2-cyanoethyl, 2-cyanopropyl, 2-cyanobutyl, 2-cyanopentyl, 2-cyanohexyl, 2-(thiocyano)ethyl, 2-(thiocyano)propyl, 2-(thiocyano)butyl, or the group

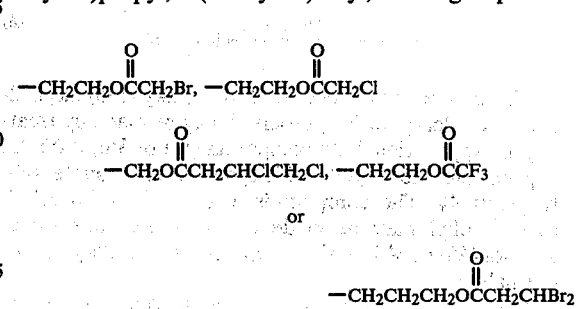

Preferably, Y is 2-haloalkyl of 2 to 6 carbon atoms, 2-hydroxyalkyl of 2 to 6 carbon atoms or 2-alkoxyalkyl of 3 to 6 carbon atoms. Most preferably Y is 2-haloalkyl of 2 to 6 carbon atoms, especially 2-haloethyl.

Preferably, W is oxygen.

Representative Z groups are methoxy, ethoxy, propoxy, butoxy, pentoxy, hexoxy, methylthio, ethylthio, propylthio, butylthio, methylamino, and dimethylamino, vinylamino, allylamino, allylmethylamino, propargylamino, methylpropargylamino, dipropargylamino, ethylpropargylamino. Preferably, Z is a substituted amino group, most preferably alkylamino. Most preferably Z is methylamino.

The compounds of my invention may be made according to the following schemes:

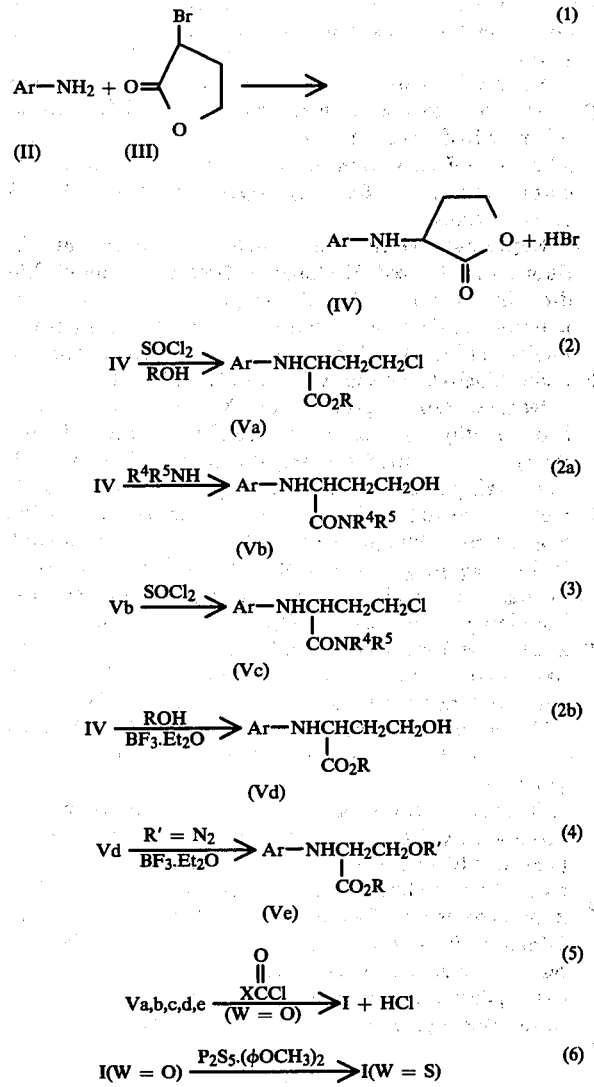

The compounds wherein Y is 2-(alkylthio)alkyl, 2-(thiocyano)alkyl or 2-cyanoalkyl may be made by treating the appropriate halo compound (Va or Vc) with the appropriate mercaptide, thiocyanate, or cyanate salt, respectively. The compounds wherein Y is haloalkylcarboxyalkyl may be made by acylating appropriate alcohol (Vb or Vd) with an appropriate haloalkylcarbonyl halide.

The alkylation reaction (1) may be conducted in the presence of a base. Suitable bases are inorganic alkali metal carbonates such as sodium carbonates or potassium carbonates or organic amines such as trialkyl amines, e.g., triethyl amine or pyridine compounds, e.g. pyridine or 2,6-dimethylpyridine. Generally, substantially equal molar amounts of the reactants (II) and (III) and the base are employed. In one modification of the reaction, a molar excess of the aniline reactant (II) is used as the base, and no additional base is employed. The reaction is conducted in inert organic solvents, e.g., apolar diprotic solvents such as dimethylformamide and acetonitrile and aromatic hydrocarbons such as benzene and toluene. The reaction temperature may vary from 25°–150° C., preferably from 50°–150° C. Water may be employed as a cosolvent. The reaction pressure may be atmospheric, subatmospheric or superatmospheric. However, for convenience of conducting the reaction of the pressure is generally atmospheric. The reaction time will, of course, vary depending upon the reactants and the reaction temperature. Generally, the reaction time is from 0.25 to 24 hours. The product (IV) is generally purified by conventional procedures, e.g., extraction, distillation or crystallization. Before use in the subsequent ring opening reactions (2), (2a), or (2b).

Selected Y and Z substituents may be obtained by employing the appropriate ring opening reaction as depicted above in (2), (2a), and (2b). Opening the lactone ring with thionyl chloride and alcohol yields, the haloester (Va). Opening the lactone with an amine yields the alcohol amide (Vb) while opening the lactone ring with alcohol and borontrifluoride etherate yields the alcohol ester (Vd). The alcohol amide (Vb) may then be converted to its corresponding haloamide (Vc) by treatment with thionyl chloride. The alcohol ester (Vd) may be converted to its corresponding ether ester (Ve) by treatment with diazoalkane and borontrifluoride etherate. Any of the intermediates Va through Ve may then be converted to the products of the invention by acylation with the appropriate acid chloride as shown in reaction (5).

The acylation reaction (5) is conducted by known conventional procedures. The arylamine (V) and the acid chloride are generally contacted in substantially equimolar amounts in inert solvents at a temperature of 0°–100° C. Suitable inert inorganic solvents include ethylacetate, methylene dichloride, dimethoxyethane, benzene, etc. The product (I, W=O) is isolated and purified by conventional procedures such as extraction, distillation, chromatography, crystallization, etc. Inorganic amines such as trialkylamine or pyridine may be employed as an acid acceptor during the acylation reaction (5).

The carbonyl product (I, W=O) may be converted to the thiono analog (I, W=S) according to the procedure (Reaction 6) described by Shridhar et al., *Organic Preparations and Procedures International*, Volume 12, pages 203–206 (1980), which is incorporated herein by reference in its entirety.

UTILITY

The compounds of the invention are useful for controlling fungi, particularly plant fungal infections. However, some fungicidal compositions of the invention may be more fungicidally active than others against particular fungi. For example, the activity of the preferred compounds of the invention is highly specific for certain fungal diseases such as downy mildews, e.g., *Plasmopara viticola* (grapes) and *Peronospora parasitica* (cabbage and collard), late blights, e.g., *Phytophthora infestans* (tomatoes and potatoes), and crown and root rots, e.g., Phytophthora.

The compounds of the invention are particularly useful fungicides because they cure established fungal infections. This permits economical use of the fungicides of the invention, because they need not be applied to plants unless fungal infection actually occurs. Thus, a preventative program of applying fungicides against potential fungal infection is not necessary.

When used as fungicides, the compounds of the invention are applied in fungicidally effective amounts to fungi and/or their habitats, such as vegetative hosts and nonvegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, for example: the aryl and alkylaryl sulfonates and their sodium salts, alkylamide sulfonates, including fatty methyl taurides; alkylaryl polyether alcohols, sulfated higher alcohols and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1–15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetrating of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators fertilizers, etc.

EXAMPLE 1

The preparation of N-[1-(2'-chloroethyl)-N',N'-dimethylamidomethyl]-N-chloroacetyl-2,6-dimethylaniline A. 3-(2,6-dimethylanilino)-gamma-butyrolactone 50 g) and 1,2-dimethoxyethane (350 ml) were stirred and 30.1 g of dimethylamine hydrate (40%) was added rapidly. The solution was allowed to stand at room temperature overnight, after which time 3.0 g of dimethylamine hydrate was added and stirring was continued for 7 hours. An additional 3.0 g of dimethylamine hydrate was added and the solution was allowed to stand again overnight, and stripped of solvent. The resultant oily residue was dissolved in 250 ml methylene chloride and washed with water (250 ml×2) dried ($MgSO_4$). The organic solution was filtered and stripped to give an oily residue which crystallized on standing. This solid was triturated with ethyl ether/petroleum ether at ice water temperature. The mixture was filtered and the solid was washed with cold petroleum ether to yield N-[1-(2'-hydroxyethyl)-N'N'-dimethylamidomethyl]-2,6-dimethylaniline, melting point 82°–84° C.

B. The product from Step A (10 g) and N,N-dimethylformamide (2 drops) in methylene chloride was stirred while thionyl chloride (4.8 g) was added over a period of 5 minutes. The solution was stirred at room temperature overnight. Then saturated sodium bicarbonate solution (100 ml) was added to the methylene chloride solution with stirring, and after cessation of evolution of gas, the organic phase was separated and collected, washed with water (100 ml), and dried ($MgSO_4$). The methylene chloride solution was filtered and the filtrate was stripped in vacuo to yield an oil. The oil was crystallized from petroleum ethers/ethyl ether, filtered, and washed with petroleum ether/ethyl ether. The mother liquor was stripped in vacuo to yield a second crop of solid which was triturated with petroleum ether/ethyl ether. A total of 7.6 g of N-[1-(2'-chloroethyl)-N',N'-dimethylamidomethyl]-2,6-dimethylaniline was obtained.

C. The product from Step B above (7.6 g) was stirred with 2.5 g of pyridine and 150 ml ethyl acetate at room temperature. To this solution 3.7 g of chloroacetyl chloride was added over a period of 5 minutes. After stirring for 1¼ hour, the solution was allowed to stand overnight at room temperature. Water (100 ml) was added to this solution, and the organic layer was separated and collected, washed with saturated sodium bicarbonate solution (100 ml), saturated sodium chloride solution (50 ml)

and dried over magnesium sulfate. The organic solution was filtered, and the filtrate was stripped in vacuo to yield an oil which crystallized from ethyl ether at dry ice temperature. This solid was triturated with petroleum ether which was filtered to give 9.2 g of solid product identified as the title product by infrared analysis and elemental analysis. Melting point 93°–94° C.

EXAMPLE 2

Preparation of
N-[1-(2'-methoxyethyl)-carbomethoxymethyl]-N-methoxyacetyl-2,6-dimethylaniline A. A stirred solution of 3-(2,6-dimethylanilino)-gamma-butyrolactone and borontrifluoride etherate (35.5 ml) in 500 ml methanol was kept at reflux at 43½ hours. The solvent was stripped in vacuo at 47° C. to yield an amber oil. The oil was dissolved in methylene chloride (200 ml) and washed with sodium bicarbonate solution (2×100 ml) and dried over in MgSO$_4$. The methylene chloride solvent was stripped in vacuo to yield an amber oil, N-[1-(2'-hydroxyethyl-carbomethoxymethyl]-2,6-dimethylaniline.

B. N-methyl-N-nitro-N-nitrosoguanidine (25 g) was added slowly to a mixture of 75 ml 40% aqueous potassium hydroxide and 300 ml ethyl ether at ice-ethanol temperature (−10°–0° C.). After addition, the yellow ethereal solution was decanted off the aqueous layer. The ethereal solution was added quickly to a stirred solution of the product from Step A above in 300 ml ethyl ether and 150 ml dichloromethane over an ice-ethanol bath. The solution was set aside at room temperature overnight. The reaction mixture was treated with 2 ml glacial acetic acid to destroy excess diazomethane. The solution was then stripped in vacuo and dissolved in a small amount of dichloromethane. The clear solution was washed with 200 ml saturated sodium bicarbonate solution and dried over MgSO$_4$. The solvent was stripped in vacuo to give 68 g of amber oil which was dissolved in diethylether and chromatographed on silica gel (700 g) and eluted with petroleum ether/diethyl ether. One fraction was collected containing the desired product and its O,N-dimethylated adduct and the second fraction was collected containing the desired product and N-methylated started material. These two fractions were combined in ethyl ether, dried (MgSO$_4$) and stripped to yield 9.1 g of oil. Infrared and nmr spectroscopy showed that this combined fraction contained the desired product, N-[1-(2'-methoxyethyl)-carbomethoxymethyl]-2,6-dimethylaniline (70%), as well as two minor impurities: N-methyl-N-(3-gamma-butyrolactone)-2,6-dimethylaniline (21%) and N-methyl-N-[1-(2'methoxyethyl)carbomethoxymethyl]-2,6-dimethylaniline (9%).

C. To a solution of a product mixture from Step B above (4.5 g) in pyridine (1 g) and ethyl acetate (50 ml) was rapidly added 1.4 g of chloroacetyl chloride. The slurry was kept at reflux for 1 hour after which time an additional 0.5 g of pyridine and 0.7 g of chloroacetyl chloride were added. After an additional hour of reflux, the reaction mixture was cooled and washed successively with water (50 ml), saturated bicarbonate solution (25 ml) and dried (MgSO$_4$). The organic solvent was stripped in vacuo to yield an oil which was chromatographed on silica gel (120 g and eluted with petroleum ether/ethyl ether. The product-containing residue was dissolved in ethyl ether, dried (MgSO$_4$), stripped to yield a clear oil (3.6 g), which was shown by infrared and nmr spectroscopy and analysis to be the desired product, N-[1-(2'methoxyethyl)-carbomethoxymethyl]-N-chloroacetyl-2,6-dimethylaniline.

EXAMPLE 3

Preparation of
N-[1-(2'-chloroethyl)-N'-methylamidomethyl]-N-methoxyacetyl-2,6-dimethylaniline A. 3-(2,6-dimethylanilino)-gamma-butyrolactone was acylated with methoxyacetyl chloride according to the procedure described in Example 2C above to yield N-methoxyacetyl-3-(2,6-dimethylanilino)-gamma-butyrolactone.

B. The stirred slurry of the product of Step A above (29.8 g) in 300 ml 1,2-dimethoxyethane at ice bath temperature was saturated with methylamine (gas). Water (20 ml) was added to the mixture and passage of methylamine was continued at room temperature for 3½ hours. The mixture was kept at room temperature overnight after saturation with excess methylamine. The solvent was stripped in vacuo to yield a solid residue which was dissolved in dichloromethane, then dried over magnesium sulfate. This solution was filtered and the filtrate was stripped in vacuo to yield a solid residue. The solid residue was triturated with ethyl ether/petroleum ether to yield a colorless solid, melting point 145°–146° C., 33.8 g, shown to be N-[1-(2'-hydroxyethyl)-N'-methylamidomethyl]-N-methoxyacetyl-2,6-dimethylaniline. To a stirred solution of the product from Step B above (30.3 g) in 300 ml 1,2-dimethoxyethane heated to reflux was added dropwise 12.0 g of thionyl chloride over a period of 15 minutes. The solution was kept at reflux for 3 hours, cooled and filtered. The filtrate was stripped in vacuo to give a solid residue. This residue was slurried with ethyl ether at ice bath temperatures to yield a tan crystalline solid which was then chromatographed on silica gel (500 g) which was eluted with petroleum ether/ethyl ether. The product containing fractions were combined in methylene chloride and dried over magnesium sulfate. The solvent was stripped in vacuo to give a solid residue. Trituration with ethyl ether gave a colorless solid as shown by infrared spectroscopy to contain the desired title product, melting point 115°–117° C. (27.3 g).

EXAMPLE 4—TOMATO LATE BLIGHT

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a small amount of a nonionic emulsifier. The sprayed plants were then inoculated one day later with the organism, placed in an environmental chamber and incubated at 66°–68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table I. In Table I, the test concentration is 250 ppm unless otherwise indicated by the figures in parentheses.

EXAMPLE 5—CELERY LATE BLIGHT

The celery late blight tests were conducted using celery (Utah) plants 11 weeks old. The celery late blight organism was *Septoria apii*. The celery plants were sprayed with solutions of the candidate toxicant mixed with acetone, water and a nonionic emulsifier. The plants were then inoculated with the organism and placed in an environmental chamber and incubated at 66°–68° F. in 100% relative humidity for an extended period of time (approximately 48 hours). Following the incubation the plants were allowed to dry and then were maintained in a greenhouse for approximately 14 days. The percent disease control provided by a given candidate toxicant is based on the percent disease reduction relative to untreated check plants. The results are reported in Table I.

EXAMPLE 6—GRAPE DOWNY MILDEW CONTROL

The compounds of the invention were tested for the control of the grape downy mildew organism *Plasmopara viticola*. Detached leaves, between 70 and 85 mm in diameter, of 7-week-old *Vitis vinifera* cultivar Emperor grape seedlings were used as hosts. The leaves were sprayed with a solution of the test compound in acetone. The sprayed leaves were dried, inoculated with a spore suspension of the organism, placed in a humid environmental chamber and incubated at 66°–68° F. and about 100% relative humidity. After incubation for two days, the plants were then held in a greenhouse seven to nine days; then the amount of disease control was determined. The percent disease control provided by a given test compound was based on the percent disease reduction relative to untreated check plants. The results are tabulated in Table I.

EXAMPLE 7—TOMATO EARLY BLIGHT

Compounds of the invention were tested for the control of the tomato Early Blight organism, *Alternaria solani conidia*. Tomato (variety Bonny Best) seedlings of 6 to 7 weeks old were used. The tomato plants were sprayed with a 250-ppm solution of the test compound in an acetone-and-water solution containing a small amount of a nonionic emulsifier. The sprayed plants were inoculated one day later with the organism, placed in the environmental chamber and incubated at 66°–68° F. and 100% relative humidity for 24 hours. Following the incubation, the plants were maintained in a greenhouse for about 12 days. Percent disease control was based on the percent disease development on untreated check plants. The compounds tested and the results are tabulated in Table I.

TABLE A

COMPOUNDS OF THE FORMULA

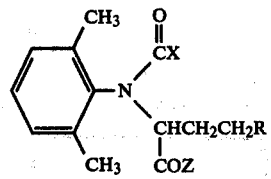

| No. | X | R | Z | mp °C. | C Cal. | C Fd. | H Cal. | H Fd. | N Cal. | N Fd. | Cl Cal. | Cl Fd. |
|---|---|---|---|---|---|---|---|---|---|---|---|---|
| 1 | CH$_2$Cl | Cl | NHCH$_3$ | 134–5 | — | — | — | — | — | — | 21.41 | 21.2 |
| 2 | " | OCOCH$_2$Cl | " | 94–95 | — | — | — | — | — | — | 18.22 | 17.9 |
| 3 | " | " | N(CH$_3$)$_2$ | 90–91 | — | — | — | — | — | — | 17.58 | 17.6 |
| 4 | " | Cl | OCH$_3$ | 81–82 | — | — | — | — | — | — | 21.41 | 20.9 |
| 5 | " | SCH$_3$ | OC$_2$H$_5$ | Oil | 8.96* | 8.1* | — | — | — | — | 90.94 | 14.1 |
| 6 | " | OCH$_3$ | OCH$_3$ | Oil | 58.62 | 58.69 | 6.76 | 6.93 | 4.27 | 3.52 | — | — |
| 7 | " | Cl | N(CH$_3$)$_2$ | 93–94 | 55.66 | 56.12 | 6.14 | 6.86 | 8.11 | 8.28 | — | — |
| 7A | " | (1) | N(CH$_3$)$_2$ | Oil | 62.23 | 61.09 | 6.85 | 7.1 | 9.07 | 8.96 | — | — |
| 8 | CH$_2$OCH$_3$ | OCH$_3$ | OCH$_3$ | Oil | 63.14 | 63.03 | 7.79 | 7.5 | 4.33 | 4.38 | — | — |
| 9 | " | OH | NHCH$_3$ | 145–146 | 62.32 | 61.63 | 7.84 | 7.78 | 9.08 | 9.12 | — | — |
| 10 | " | Cl | NHCH$_3$ | 115–117 | 58.80 | 59.31 | 7.09 | 7.02 | 8.57 | 7.82 | — | — |
| 11 | " | " | N(CH$_3$)$_2$ | 94–96 | 59.91 | 61.22 | 7.39 | 7.73 | 8.72 | 8.63 | — | — |
| 12 | " | Cl | OCH$_2$CH$_3$ | Oil | 59.73 | 58.65 | 7.08 | 7.2 | 4.10 | 3.96 | — | — |
| 13 | " | Cl | OCH$_3$ | 70–71 | 58.02 | 59.47 | 6.77 | 6.97 | 4.27 | 4.64 | — | — |
| 10A | " | H | NHCH$_3$ | 105–108 | 65.73 | 65.94 | 8.27 | 8.58 | 9.58 | 9.59 | — | — |
| 14 | CH=CHCH$_3$ | Cl | OCH$_3$ | Oil | 63.05 | 61.77 | 6.85 | 7.18 | 4.33 | 4.29 | — | — |
| 15 | CH$_2$CH=CH$_2$ | Cl | OCH$_3$ | Oil | 63.05 | 65.39 | 6.85 | 7.84 | 4.33 | 4.81 | — | — |
| 16 | CH=CHCH$_3$ | Cl | NHCH$_3$ | 138–140 | 63.26 | 63.13 | 7.16 | 7.26 | 8.68 | 8.45 | — | — |
| 17 | Cyclopropyl | Cl | NHCH$_3$ | 118–120 | 63.26 | 63.57 | 7.16 | 7.55 | 8.68 | 8.74 | — | — |
| 18 | 2-Furanyl | Cl | OCH$_3$ | 101–102 | 61.80 | 62.61 | 5.76 | 5.99 | 4.00 | 4.08 | — | — |
| 19 | 2-Furanyl | Cl | NHCH$_3$ | 128–130 | 61.98 | 61.02 | 6.07 | 6.17 | 8.03 | 7.82 | — | — |
| 19A | 2-Furanyl | (2) | — | 172–175 | 69.21 | 69.43 | 6.45 | 6.87 | 8.97 | 8.93 | — | — |
| 20 | CH$_2$CH$_2$CH$_3$ | Cl | NHCH$_3$ | — | 62.85 | 62.4 | 7.76 | 7.88 | 8.62 | 8.64 | — | — |
| 21 | CH$_2$CH$_2$\\O/CH$_3$CH$_2$ | Cl | NHCH$_3$ | — | 60.92 | 60.87 | 7.67 | 7.77 | 7.89 | 7.63 | — | — |

COMPARISON COMPOUNDS

| 22 | CH$_2$OCH$_3$ | CH$_3$ | NHCH$_3$ | Oil | 66.64 | 67.48 | 8.55 | 8.77 | 9.14 | 9.36 | — | — |

TABLE A-continued
COMPOUNDS OF THE FORMULA

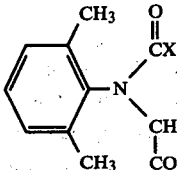

| No. | X | R | Z | mp °C. | C Cal. | C Fd. | H Cal. | H Fd. | N Cal. | N Fd. | Cl Cal. | Cl Fd. |
|---|---|---|---|---|---|---|---|---|---|---|---|---|
| 23 | CH$_2$OCH$_3$ | H | OCH$_2$CH$_3$ | 50–52 | 66.42 | 67.87 | 8.19 | 8.66 | 4.56 | 4.83 | — | — |

(1) ⟩CHCH$_2$CH$_2$R is replaced by ⟩C=CHCH$_3$ (2) ⟩CHCH$_2$CH$_2$R is replaced by 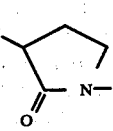
         |
        COZ

TABLE I
FUNGICIDAL ACTIVITY PERCENT CONTROL

| No. | GDM | TLB | CLB | TEB |
|---|---|---|---|---|
| 1 | — | — | 0 | 0 |
| 2 | — | — | 0 | 21 |
| 3 | — | — | 27 | 18 |
| 4 | — | 0 | 0 | 0 |
| 5 | — | 0 | 0 | 0 |
| 6 | — | 0 | 44 | — |
| 7 | 99 | 98 | — | 0 |
| 7A | 65 | 0 | 0 | 0 |
| 8 | — | 63 | 57 | 0 |
| 9 | 8 | 0 | 35 | — |
| 10 | 100 | 98 | 13 | 0 |
| 10A | 6 | 0 | 0 | 0 |
| 11 | 100 | 100 | — | 0 |
| 12 | 76 | 56 | 18 | 0 |
| 13 | 100 | 0 | 0 | 0 |
| 14 | 11 | 0 | — | 0 |
| 15 | 100 | 11 | — | 0 |
| 16 | 99 | 98 | 0 | 23 |
| 17 | 99 | 0 | 0 | 23 |
| 18 | 100 | 71 | — | 0 |
| 19 | 100 | 100 | 0 | 0 |
| 19A | 98 | 21 | 0 | 0 |
| 20 | 100 | 67 | 13 | — |
| 21 | 89 | 0 | 6 | — |
| 22 | 0 | 18 | 44 | 0 |
| 23 | 99 | 29 | 0 | 27 |

GDM = Grape Downy Mildew (*Plasmopara viticola*)
TBL = Tomato Late Blight (*Phytophthora infestans*)
CLB = Celery Late Blight (*Septoria apii*)
TEB = Tomato Early Blight (*Alternaria solani*)

What is claimed is:

1. A compound having the formula:

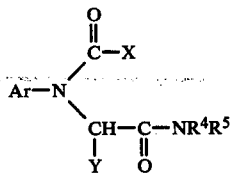

wherein
Ar is 2,6-dialkylphenyl;
R$^4$ is hydrogen, alkyl of 1 to 4 carbon atoms, alkenyl of 2 to 4 carbon atoms or alkynyl of 2 to 4 carbon atoms;
R$^5$ is hydrogen or alkyl of 1 to 4 carbon atoms;
X is alkoxyalkyl of 2 to 12 carbon atoms; and
Y is 2-haloalkyl of 2 to 6 carbon atoms, 2-hydroxyalkyl of 2 to 6 carbon atoms or 2-alkoxyalkyl of 2 to 12 carbon atoms.

2. The compound according to claim 1 wherein X is methoxymethyl, Y is 2-chloroethyl, R$^1$, R$^2$ and R$^4$ are methyl and R$^5$ is hydrogen.

3. The compound according to claim 1 wherein X is methoxymethyl, Y is 2-chloroethyl, and R$^1$, R$^2$, R$^4$ and R$^5$ are methyl.

4. A fungicidal composition comprising a biologically inert carrier and a fungicidally effective amount of a compound defined in claim 1.

5. A method for the control of plant fungi which comprises applying to said fungi or their plant hosts a fungicidally effective amount of a compound defined in claim 1.

6. A method for the control of *Plasmopara viticola* fungi which comprises applying to said fungi or their plant hosts a fungicidally effective amount of a compound defined in claim 1.

7. A method for the control of *Phytophthora infestans* fungi which comprises applying to said fungi or their plant hosts a fungicidally effective amount of a compound defined in claim 1.

* * * * *